(12) United States Patent
O'Keefe et al.

(10) Patent No.: US 10,266,554 B2
(45) Date of Patent: Apr. 23, 2019

(54) PREPARATION OF ISOCYANATOSILANES

(71) Applicant: Momentive Performance Materials Inc., Waterford, NY (US)

(72) Inventors: Brendan John O'Keefe, Waterford, NY (US); Roland Wagner, Bonn (DE); Holger Jürgen Glatzer, Leverkusen (DE); Tiberiu Simandan, Termoli (IT); Konstantin Kraushaar, Freiberg (DE); Joe Adrian Biele, Freiberg (DE); Edwin Kroke, Halsbrücke (DE)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/609,182

(22) Filed: May 31, 2017

(65) Prior Publication Data

US 2018/0346493 A1 Dec. 6, 2018

(51) Int. Cl.
*C07F 7/18* (2006.01)

(52) U.S. Cl.
CPC .................. *C07F 7/1876* (2013.01)

(58) Field of Classification Search
None
See application file for complete search history.

(56) References Cited

U.S. PATENT DOCUMENTS

| | | |
|---|---|---|
| 3,511,866 A | 5/1970 | Pepe et al. |
| 3,895,076 A | 7/1975 | Bauer et al. |
| 4,414,376 A * | 11/1983 | Siedle ............ C07F 7/14 525/100 |
| 4,778,905 A | 10/1988 | Besson et al. |
| 4,820,674 A * | 4/1989 | Shiozawa ......... B01J 31/0204 502/169 |
| 4,999,443 A | 3/1991 | Bertleff et al. |
| 5,616,762 A | 4/1997 | Kropfgans et al. |
| 7,825,243 B2 | 11/2010 | Childress et al. |
| 9,000,220 B2 | 4/2015 | Christiansen et al. |
| 9,309,271 B2 | 4/2016 | Simandan et al. |
| 2010/0048932 A1 | 2/2010 | Marciniec et al. |

FOREIGN PATENT DOCUMENTS

| | | |
|---|---|---|
| JP | 55040592 | 5/1977 |
| JP | 2008074804 | 3/2008 |

OTHER PUBLICATIONS

International Search Report dated May 24, 2018.
Hewitt et al. Synthesis of A-alkyl-A-aminosilanes by rhodium-catalyzed hydrosilyation of Boc-protected vinyl amines, Journal, Jul. 24, 2000, pp. 10175-10179, Elsevier Science Ltd.
Haehyun Nam et al: Functional Organotrimethoxysilane Derivative with Strong Intermolecular (pi]-[pi] Interaction: One-Pot Grafting Reaction on Oxidized Silicon Substrates, Langmuir, vol. 22, No. 17, Jun. 13, 2006 (Jun. 13, 2006), pp. 7132-7134.

* cited by examiner

*Primary Examiner* — Clinton A Brooks
(74) *Attorney, Agent, or Firm* — James C. Abruzzo

(57) ABSTRACT

There is provided herein a method of preparing an isocyanatosilane including reacting an olefinic isocyanate with a hydridosilane in the presence of a dinuclear rhodium complex under hydrosilylation conditions.

21 Claims, No Drawings

PREPARATION OF ISOCYANATOSILANES

FIELD OF THE INVENTION

The invention is directed to methods of producing isocyanatosilanes, more specifically, methods employing rhodium catalysts.

BACKGROUND OF THE INVENTION

Isocyanatosilanes are well-known silicon-containing materials which have long been used in the production of other silicon-containing products such as in the production of polyurethanes, e.g., polyurethanes used in the building and construction fields. Unfortunately, isocyanatosilanes tend to have a high manufacturing cost, which limits their potential applications. For instance, 3-isocyanatopropylalkoxysilanes are used as end-cappers in the preparation of silylated polymers. Even though 3-isocyanatopropylalkoxysilanes are used in small quantities, their high cost significantly increases the total cost of silylated polymers and the products made from them. Various methods are known for preparing isocyanatosilanes, all of which suffer from drawbacks that result in a high cost or other undesired features of the produced isocyanatosilanes. Such known methods of making isocyanatosilanes include:

1. Formation of isocyanatosilane by the thermal cleavage (or cracking) of a carbamatosilane (along with formation of the by-product alcohol);
2. Formation of isocyanatosilane via the reaction of haloalkylsilane with metal cyanate;
3. Formation of isocyanatosilane via the reaction of aminosilane with phosgene:
4. Formation of isocyanatosilane via the hydrosilylation of allyl isocyanate with hydridosilane.

Method 1 typically involves multiple steps to first prepare the carbamatosilane, followed by the relatively inefficient cracking of the carbamate into isocyanatosilane.

Method 2 has the drawback of low yields of isocyanatosilane when the reaction is performed due to significant trimerization of the formed isocyanatosilane, resulting in the formation of by-product isocyanurate.

Method 3 involves the handling of dangerous phosgene gas and requires the efficient scavenging of acid by-products formed during the course of the reaction.

Method 4 has been unattractive due to low yields, high reaction temperature, long reaction time and the formation of unwanted by-products.

There thus remains a desire in the industry for a process for the synthesis of isocyanatosilanes yielding the target molecules in high yield, without major by-products, such as cyanurates or undesired high molecular weight species, based on large scale and economically accessible raw materials, and avoiding the use of regulated compounds, such as phosgene.

SUMMARY OF THE INVENTION

In one non-limiting embodiment herein there is provided an improved process for making isocyanatosilanes in high yield, at low reaction temperature, with a short reaction time and limited formation of by-products.

There is provided herein a method of preparing an isocyanatosilane comprising reacting an olefinic isocyanate with a hydridosilane in the presence of a dinuclear rhodium complex under hydrosilylation conditions.

DETAILED DESCRIPTION OF THE INVENTION

The present invention relates to an improved process for preparing isocyanatosilanes which can be conducted at low reaction temperature, in a short reaction time, delivering a high yield, with a significantly decreased level of undesired by-products such as isocyanurate, and which also avoids the problems from previous processes.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

As used in the claims, the word "comprises" and its grammatical variants logically also subtend and include phrases of varying and differing extent such as for example, "consisting essentially of" and "consisting of".

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

It will be understood herein that in one non-limiting embodiment, any definition of any one or more of R, R^, R', R'', $R^1$, $R^2$, X, $L^1$, $L^2$, $L^3$, a, n, x, y and z can also have the same definition in any formulae that appear herein that contain such variables or subscripts.

As used herein the term "alkyl" means a monovalent saturated straight or branched hydrocarbon radical. In a preferred embodiment, alkyl groups are selected from linear or branched alkyl groups containing from 1 to 60 carbons per group, such as, for example, methyl, ethyl, n-propyl, iso-propyl, n-butyl, iso-butyl, sec-butyl, tert-butyl, pentyl, hexyl, heptyl, decyl, dodecyl.

As used herein the term "alkenyl" means a monovalent straight or branched unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology of any of "cycloalkyl hydrocarbon radical" "cyclic alkyl", "cycloalkyl" each means a monovalent radical containing one or more saturated hydrocarbon rings, specifically containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable cycloalkyl hydrocarbon radicals include, for example, cyclohexyl and cyclooctyl, 1-dimethylene-2,4-cyclohexyl, 1-methylethylene-3-methyl-3,4-cyclohexyl, and the like.

As used herein, the terminology "aromatic hydrocarbon radical" means a monovalent hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl, 1,2-phenylene, 1,4-phenylene, 4-methyl-1,2-phenylene, phenylmethylene, 1-trimethylene-3,5-phenylene, and the like.

The terms "alkyl", "alkenyl", "cycloalkyl", and "aromatic" as defined above are understood to be the respective ordinary meanings of these terms to a person of ordinary skill in the art, however, it shall be understood herein that when such terms are used to define various ligands in the rhodium dinuclear complex described herein, that such moieties can also be divalent, or polyvalent i.e., 3 or more valences, as is understood by those skilled in the art of metal complexes.

In addition, it will be understood herein that the use of ranges of such as "up to" a certain number of carbon atoms are used for expediency to define, e.g., a carbon atom range for both alkyls, alkenyl, cycloalkyls, aromatics and the like, which each can have different conventionally understood minimum numbers of carbon atoms, e.g., alkyl can have 1 carbon atoms, while alkenyls must have at least two carbon atoms, and cycloalkyls and aromatic groups generally have at least 5 carbon atoms, and as such, these lower understood limits can be used in any applicable range described herein of such moieties or such moieties can contain a minimum number of carbon atoms as is understood by those skilled in the art for such a group.

The term "heteroatom" as used herein can be any one of O, N, S, P, and the like, which heteroatom can be present alone as one atom, or in a moiety wherein one or more of said same or different heteroatoms are present, such as the non-limiting examples of a carboxylate moiety (—R—C(=O)O$^-$), an amide moiety (RR'N$^-$), sulfonamide (R—S(=O)$_2$—NRR'), and a phosphoramide ($R_2$—P(=O)—NR'$_2$), wherein R and R' are organic moieties such as alkyl, alkenyl, aryl, aralkyl, cycloalkyl, and the like containing up to 60 carbon atoms. It will be understood herein that any definition containing a heteroatom as described herein can comprise one or more of the same and/or different heteroatom groups in the respective hydrocarbyl, hydrocarbon, or organic group defined herein.

In a non-limiting embodiment herein there is provided a method for the preparation of the isocyanatosilane of the general formula (I):

$$(R^1O)_{3-n}(R^2)_n Si-R-NCO \quad (I)$$

where R is a divalent hydrocarbyl group containing up to 12 carbon atoms, e.g., a divalent alkyl group such as defined above, and more preferably up to about 8 carbon atoms, and optionally containing at least one heteroatom, where $R^1$ and $R^2$ are each independently a linear or branched alkyl, cycloalkyl or aromatic group containing up to 12 carbon atoms, preferably up to 8 carbon atoms, and most preferably up to 6 carbon atoms, and where the subscript n is an integer of from 0 to 3, preferably zero or 1.

In another embodiment herein the isocyanatosilane produced in the method described herein is selected from the group consisting of 3-isocyanatopropyltrimethoxysilane, 2-isocyanato-1-methylethyltrimethoxysilane, 2-isocyanatopropyltrimethoxysilane, 4-isocyanatobutyltrimethoxysilane, 2-isocyanato-1,1-dimethylethyltrimethoxysilane, 3-isocyanatopropyltriethoxysilane, 2-isocyanato-1-methylethyltriethoxysilane, 2-isocyanatopropyltriethoxysilane, 4-isocyanatobutyltriethoxysilane, 2-isocyanato-1,1-dimethylethyltriethoxysilane, 3-isocyanatopropylmethyldimethoxysilane, 3-isocyanatopropylmethyldiethoxysilane, 2-isocyanato-1-methylethylmethyldimethoxysilane, 2-isocyanatopropylmethyldimethoxysilane, 4-isocyanatobutylphenyldimethoxysilane, and combinations thereof.

The isocyanatosilane of formula (I) can be produced by the following non-limiting reaction:

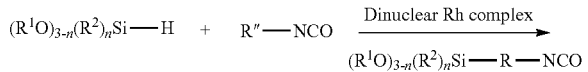

wherein R, $R^1$, $R^2$, R'' and n are as defined herein.

The olefinic isocyanate which is employed in the method herein can be of the general formula (II):

$$R''\text{—NCO} \quad (II)$$

wherein R" is a linear, branched, cyclic or aromatic monovalent olefinic hydrocarbyl group containing up to about 12 carbon atoms, preferably up to 8 carbon atoms, and most preferably up to 6 carbon atoms, and each optionally having at least one heteroatom.

In one non-limiting embodiment herein the olefinic isocyanate is selected from the group consisting of vinyl isocyanate, allyl isocyanate, 3-isocyanato-2-methyl-propene, vinylbenzylisocyanate, 1-isocyanato-2-butene, 1-isocyanato-3-methyl-2-butene, 3-isocyanato-1-butene, 3-isocyanato-3-methyl-1-butene, 3-isocyanato-2,3-dimethyl-1-butene, 4-isocyanato-2-methyl-1-butene, 4-isocyanato-3,3-dimethyl-1-butene, 3-isocyanato-3-methyl-1-pentene, 4-isocyanato-4-methyl-1-pentene, 5-isocyanato-1-pentene, 3-isocyanato-1-hexene, 3-isocyanato-5,5-dimethyl-1-hexene, 1-isocyanato-2-heptene and combinations thereof.

In another embodiment herein, the hydridosilane can be of the general formula (III):

$$(R^1O)_{3-n}(R^2)_n Si\text{—H} \quad (III)$$

wherein $R^1$ and $R^2$ are each independently a linear or branched alkyl, cycloalkyl or aromatic group containing up to 12 carbon atoms, preferably up to 8 carbon atoms, and most preferably up to 6 carbon atoms, and where the subscript n is an integer of from 0 to 3, preferably 0 or 1.

In one embodiment the hydridosilane is selected from the group consisting of trimethoxysilane, triethoxysilane, tripropoxysilane, tri-iso-propoxysilane, tributoxysilane, tri-iso-butoxysilane, methyldiethoxysilane, methyldimethoxysilane, dimethylethoxysilane, dimethylmethoxysilane, cyclohexyldi-iso-propoxysilane, phenyldimethoxysilane, and combinations thereof.

The dinuclear rhodium complex employed in the method herein can be any dinuclear rhodium complex or combination of any dinuclear rhodium complexes. In one non-limiting embodiment described herein, the dinuclear rhodium complex can be of the general formula (IV):

$$Rh_2(\mu\text{-}X)_a L^1_x L^2_y L^3_z \quad (IV)$$

wherein each of $L^1$, $L^2$, $L^3$ and X are ligands selected from the group consisting of Cl, Br, I, OH, R^, OR^, OSiR^$_3$, H, CO, R^C(=O)O, O, SR^, S, Se, CO$_3$, SO$_3$, SO$_4$, HPO$_4$, R^PO$_4$, CN, NCO, NCS, NO$_2$, NO$_3$, ClO$_4$, R^SO$_4$, phosphonate, phosphinate, phosphine, amine, imine, amide, amine, nitrile, heterocycle, β-diketonate, β-diketiminate, amidinate, sulfonate, olefin, ether, thioether, isonitrile, R^NCO, R^NCS, R^OCN, sulfoxide, amineoxide, SO$_2$, CO$_2$, NO, wherein each R^ is independently a linear, branched, cyclic or aromatic hydrocarbon moiety which contains up to 16 carbon atoms, preferably up to 12 carbon atoms, more preferably up to 8 carbon atoms and most preferably up to 6 carbon atoms, and optionally at least one heteroatom, and combinations of two or more of the foregoing ligands which are incorporated into a single ligand, provided that X is a bridging ligand bridging the two rhodium atoms, and where the subscript a is an integer of from 1 to 8, preferably 1-4, more preferably 2, and the subscripts x, y and z are each independently an integer of from 0 to 8, preferably from 1-4, more preferably wherein x+y+z=2 or 4.

In one embodiment herein, each of $L^1$, $L^2$ and $L^3$ can be selected from the group consisting of alkyl groups such as methyl and ethyl, aryl groups such as phenyl, arene groups such as benzene, cyclopentadienes such as cyclopentadienyl and pentamethylcyclopentadienyl, alkyne groups such as 2-butyne, 3-hexyne and 4-octyne —OR^ groups such as methoxy, ethoxy, n-propoxy, iso-propoxy, butoxy and tert-butoxy, —OSiR^$_3$ groups such as —OSiMe$_3$, —OSiEt$_3$, and —OSiPh$_3$, wherein Me is methyl, Et is ethyl and Ph is phenyl, carboxylate groups such as acetate, hexanoate, ethylhexanoate, octanoate, neodecanoate, trifluoroacetate and triphenylacetate, SR^ groups such as SMe, SEt, SPr, and SBu, wherein Me and Et are as defined, and Pr is propyl and Bu is butyl, ether groups such as dimethyl ether and diethyl ether, thioether groups such as dimethyl thioether, diethyl thioether phosphine groups such as triphenylphosphine, 1,4-bis(diphenylphosphino)butane, and 1,2-bis(diphenylphosphino)ethane, amine groups such as hexylamine and dibutylamine, imine groups such as N-salicylideneaniline, N,N'-bis(2-aminobenzal)ethylenediamine, and N,N'-ethylenebis(salicylimine), amide groups such as dimethylamide, diethylamide, dipropylamide, and di-iso-propylamide, heterocycle groups such as pyridine, tetrahydrofuran, imidazole and β-diketonate groups, such as acetylacetonate, hexafluoroacetylacetonate and trifluoroacetylacetonate, nitrile groups such as acetonitrile and benzonitrile, olefin groups such as ethylene, cyclooctene, 1,5-cyclooctadiene, norbornadiene, and 1,5-hexadiene, β-diketiminate groups such as N,N'-diphenylpentanediiminate, amidinate groups such as N,N'-di-tert-butylacetamidinate and N,N'-di-iso-propylformamidinate, sulfonate groups such as trifluoromethanesulfonate and para-toluenesulfonate, carbene groups such as 1,3-dimethylimidazol-2-ylidene and 1,3-di-tert-butylimidazol-2-ylidene, and the carbonyl group CO.

The use of the greek letter mu "μ" in the dinuclear rhodium complex formulae described herein is understood by those skilled in the art to signify that the X ligand bonded thereto, i.e., μ-X, is a bridging ligand bridging between the two rhodium atoms of the complex.

The aforementioned ligand groups and any of those described herein, while recited in a valence such as a monovalent, e.g., alkyl, are understood by those skilled in the art that when employed in a metal complex, such as the dinuclear metal complex described herein, can be divalent, trivalent or polyvalent as needed to meet the appropriate metal valence of the compound or salt thereof.

In one specific embodiment herein each of $L^1$, $L^2$, $L^3$ and X of general formula (IV) and those others described herein, can be a ligand selected from the group consisting of Cl, Br, I, CO, H, 1,5-cyclooctadiene, carboxylate, triphenylphosphine, benzonitrile, benzene, CN and combinations thereof.

In another specific embodiment each of the bridging ligands X are independently selected from the group consisting of Cl, Br, I, OH, OR^, OSiR^$_3$, SR^, CO, O, H, carboxylate, and combinations thereof wherein R^ is as defined. In an even more specific embodiment herein each of the bridging ligands X are selected from the group consisting of Cl, Br, I, OH, OSiR^$_3$, carboxylate, and combinations thereof.

In another embodiment herein the dinuclear rhodium complex is of the general formula (V):

$$[Rh(\mu\text{-}X)L^1_x L^2_y L^3_z]_2 \quad (V)$$

and where X, $L^1$, $L^2$, $L^3$ are as defined, and the subscripts x, y and z are each independently an integer from 0 to 4, preferably, x+y+z=1 or 2. In one embodiment, formula (V) is a species of formula (IV), where the rhodium complex is a dimer. In one embodiment of general formula (V), the bridging ligand X is selected from the group consisting of Cl, Br, I, OH, R^, OR^, OSiR^$_3$, SR^, CO, O, H, and combinations thereof where R^ is as defined. In another specific embodiment herein of general formula (V), X is Cl and each of $L^1$, $L^2$, and $L^3$ are each independently selected from the group consisting of 1,5-cyclooctadiene, CO, norbornadiene, ethylene, cyclooctene, 1,5-hexadiene and triphenylphosphine and R^ is as defined.

The dinuclear rhodium complexes described herein can be selected from the group consisting of $Rh_2Cl_2(CO)_4$, $Rh_2Cl_2(cod)_2$, $Rh_2Br_2(CO)_4$, $Rh_2I_2(CO)_4$, $Rh_2Cl_2(nbd)_2$, $Rh_2Cl_2(C_2H_4)_4$, $Rh_2Cl_2(coe)_4$, $Rh_2Cl_2(hde)_2$, $Rh_2Cl_2(PPh_3)_4$, $Rh_2Cl_2(CO)_2(PPh_3)_2$, $Rh_2Cl_4(Cp^*)_2$, $Rh_2Br_2(cod)_2$, $Rh_2I_2(cod)_2$, $Rh_2(OH)_2(cod)_2$, $Rh_2(OCH_3)_2(cod)_2$ and $Rh_2(OSiCH_3)_2(cod)_2$, wherein "cod" is 1,5-cyclooctadiene, "nbd" is 2,5-norbornadiene, "coe" is cyclooctene, "hde" is 1,5-hexadiene, "$PPh_3$" is triphenylphosphine, and "$Cp^*$" is pentamethylcyclopentadienyl.

In another embodiment herein the dinuclear rhodium complex is an asymmetrical dinuclear rhodium complex of the general formula (VI):

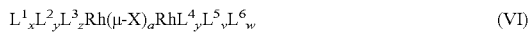

$$L^1_x L^2_y L^3_z Rh(\mu-X)_a RhL^4_u L^5_v L^6_w \quad \text{(VI)}$$

wherein $L^1$, $L^2$, $L^3$, and a, x, y and z are as defined, and each of $L^4$, $L^5$ and $L^6$ are as defined for each of $L^1$, $L^2$, $L^3$, and the subscripts u, v and w are each as defined for each of x, y and z, and preferably, x+y+z=1 or 2, and u+v+w=1 or 2, such as the non-limiting example of $(CO)_2Rh(\mu-Cl)_2Rh(CO)(coe)$.

The hydrosilylation conditions used in the method described herein can be any of those commercially known to those skilled in the art, and generally can comprise a temperature of from about 50° C. to about 150° C., more specifically from about 70° C. to about 120° C. and most specifically from about 80° C. to about 100° C., and/or for a period of time of from about 1 h to about 8 h, more specifically from about 1.5 h to about 5 h and most specifically from about 2 h to about 2.5 h, at ambient pressure. Due to the use of the dinuclear rhodium complexes described herein, such hydrosilylation temperature of the present invention can generally be from about 20 to about 40 degrees less than conventional hydrosilylation conditions for reacting the same reactants as described in the method herein but utilizing a mononuclear metal complex, such as a mononuclear rhodium complex (see Comparative Examples 1 and 2). In addition, due to the use of the dinuclear rhodium complex described herein, the hydrosilylation time period of the present invention can generally be from about 16 to about 22 hours less than conventional hydrosilylation conditions for reacting the same reactants as described in the method herein but utilizing a mononuclear metal complex, such as a mononuclear rhodium complex.

In one embodiment herein the isocyanatosilane made by the method described herein can have a purity of from about 1% to about 95%, preferably from about 85% to about 95% based on the total weight of the reaction product, immediately following the reaction and prior to any purification step(s). In another embodiment, the isocyanatosilane made by the method described herein can be in the substantial absence of an isocyanurate byproduct concentration, such as in an amount of less than 10% and more specifically, less than 5%, based on the weight of the reaction product as determined immediately after the production of the isocyanatosilane or at a period of at about 5 days thereafter.

In an embodiment herein in the method described for making the isocyanatosilane of the general formula (I) after the hydrosilylation of the compound of formula (II) with the compound of formula (III), in the presence of the dinuclear rhodium complex, the method can further comprise purifying the isocyanatosilane of the formula (I) from the reaction product mixture. Any conventional method of purification can be used, such as filtration, extraction, distillation and the like. Some more specific methods of purifying the reaction product mixture can comprise thin film evaporation, pre-evaporation, a vapor-liquid separation, a packed bed column distillation, a rotary thin film evaporation and an evaporator-stripper purification.

EXAMPLES ppm=parts per million by weight
cod=1,5-cyclooctadiene
$Ph_3P$=triphenylphosphine
PhCN=benzonitrile
All syntheses and manipulations were performed in Schlenk-type glassware or in a glovebox (MBraun, Germany, $O_2$<0.1 ppm, $H_2O$<0.1 ppm) under argon or nitrogen atmosphere.

Example 1

Reaction using the dinuclear rhodium complex $Rh_2Cl_2(CO)_4$ as catalyst to prepare 3-isocyanatopropyl trimethoxysilane:

A 10 mL Schlenk round bottom flask was equipped with a magnetic stir bar, reflux condenser and 1.8 mg (386 ppm Rh) of $Rh_2Cl_2(CO)_4$ (Acros Organics). 1.53 mL (1.47 g; 12.04 mmol) Trimethoxysilane (Sigma-Aldrich) and 1.06 mL (1.00 g; 12.04 mmol) allyl isocyanate (Sigma-Aldrich) were added via syringes. The solution was stirred and heated by an oil bath at 80° C. for 2.5 h. This crude product was pale yellow in color with purity of 95% as determined by NMR spectroscopy. The crude product was distilled at $2.7 \times 10^{-1}$ mbar. The highly volatile compounds were collected in a liquid nitrogen trap and separately 1.70 g (8.24 mmol, 68.8%) of a colorless liquid boiling at 48° C. at $2.7 \times 10^{-1}$ mbar was obtained. This product was determined to be the desired 3-isocyanatopropyltrimethoxysilane by $^{29}$Si-, $^1$H- and $^{13}$C-NMR spectroscopy.

Example 2

Reaction using the dinuclear rhodium complex $Rh_2Cl_2(cod)_2$ as catalyst to prepare 3-isocyanatopropyltrimethoxysilane:

A 10 mL Schlenk round bottom flask was equipped with a magnetic stir bar, reflux condenser and 0.7 mg (118 ppm Rh) of $Rh_2Cl_2(cod)_2$ (Sigma-Aldrich). 1.53 mL (1.47 g; 12.04 mmol) Trimethoxysilane (Sigma-Aldrich) and 1.06 mL (1.00 g; 12.04 mmol) allyl isocyanate (Sigma-Aldrich) were added via syringes. The solution was stirred and heated by an oil bath at 80° C. for 2.5 h. This crude product was pale yellow in color with 90% content of the desired 3-isocyanatopropyltrimethoxysilane as determined by $^{29}$Si-NMR spectroscopy.

Comparative Example 1

Reaction using the mononuclear rhodium salt $RhCl_3$ as catalyst to prepare 3-isocyanatopropyltrimethoxysilane:

A 25 mL Schlenk round bottom flask was equipped with a magnetic stir bar, reflux condenser and 5 mg (796 ppm Rh) of anhydrous $RhCl_3$ (Sigma-Aldrich). 1.92 mL (1.84 g; 15.06 mmol) Trimethoxysilane (Sigma-Aldrich) and 1.33 mL (1.25 g; 15.04 mmol) allyl isocyanate (Sigma-Aldrich) were added via syringes. The solution was stirred and heated by an oil bath at 80° C. for 2.5 h. No desired 3-isocyanatopropyltrimethoxysilane was obtained as determined by $^{29}$Si-, $^1$H- and $^{13}$C-NMR spectroscopy.

Comparative Example 2

Reaction using the mononuclear rhodium complex (Ph$_3$P)$_3$RhCl as catalyst to prepare 3-isocyanatopropyltrimethoxysilane:

A 25 mL Schlenk round bottom flask was equipped with a magnetic stir bar, reflux condenser and 20 mg (359 ppm Rh) of (Ph$_3$P)$_3$RhCl (Alfa-Aesar). 3.84 mL (3.69 g; 30.20 mmol) Trimethoxysilane (Sigma-Aldrich) and 2.66 mL (2.50 g; 30.10 mmol) allyl isocyanate (Sigma-Aldrich) were added via syringes. The solution was stirred and heated by an oil bath at 80° C. for 2.5 h. No desired 3-isocyanatopropyltrimethoxysilane was obtained as determined by $^{29}$Si-, $^1$H- and $^{13}$C-NMR spectroscopy.

Comparative Example 3

Reaction using mononuclear platinum complex PtCl$_2$(PhCN)$_2$ as catalyst to prepare 3-isocyanatopropyltrimethoxysilane:

A 10 mL Schlenk round bottom flask was equipped with a magnetic stir bar, reflux condenser and 0.8 mg (134 ppm Pt) of PtCl$_2$(PhCN)$_2$, 1.53 mL (1.47 g; 12.04 mmol) Trimethoxysilane (Sigma-Aldrich) and 1.06 mL (1.00 g; 12.04 mmol) allyl isocyanate (Sigma-Aldrich) were added via syringes. The solution was stirred and heated by an oil bath at 80° C. for 2.5 h. The crude product was colorless with 10% content of the desired 3-isocyanatopropyltrimethoxysilane as determined by $^{29}$Si-NMR spectroscopy.

Comparative Example 4

Reaction using the dinuclear ruthenium complex Ru$_2$Cl$_4$(C$_6$H$_6$)$_2$ as catalyst to prepare 3-isocyanatopropyltrimethoxysilane:

A 10 mL Schlenk round bottom flask was equipped with a magnetic stir bar, reflux condenser and 2 mg (262 ppm Ru) of Ru$_2$Cl$_4$(CH$_6$)$_2$. 1.92 mL (1.84 g; 15.06 mmol) Trimethoxysilane (Sigma-Aldrich) and 1.33 mL (1.25 g; 15.04 mmol) allyl isocyanate were added via syringes. The solution was stirred and heated by an oil bath at 80° C. for 2 h. The crude product was colorless with 5% content of the desired 3-isocyanatopropyltrimethoxysilane as determined by $^{29}$Si-NMR spectroscopy.

Comparative Example 5

Reaction using the dinuclear iridium complex Ir$_2$Cl$_2$(cod)$_2$ as catalyst to prepare 3-isocyanatopropyltrimethoxysilane:

A 10 mL Schlenk round bottom flask was equipped with a magnetic stir bar, reflux condenser and 5 mg (926 ppm Ir) of Ir$_2$Cl$_2$(cod)$_2$. 1.92 mL (1.84 g; 15.06 mmol) Trimethoxysilane (Sigma-Aldrich) and 1.33 mL (1.25 g; 15.04 mmol) allyl isocyanate (Sigma-Aldrich) were added via syringes. The solution was stirred and heated by an oil bath at 80° C. for 2 h. The crude product was pale yellow with 20% content of the desired 3-isocyanatopropyltrimethoxysilane as determined by $^{29}$Si-NMR spectroscopy.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A method of preparing an isocyanatosilane having the general formula (I):

$$(R^1O)_{3-n}(R^2)_n Si-R-NCO \quad (I)$$

wherein

R is a divalent hydrocarbyl group containing up to 12 carbon atoms and optionally containing at least one heteroatom, R$^1$ and R$^2$ are each independently a linear or branched alkyl, cycloalkyl or aromatic group containing up to 12 carbon atoms, and the subscript n is an integer of from 0 to 2 comprising reacting an olefinic isocyanate having the general formula (II):

$$R''-NCO \quad (II)$$

wherein R'' is a linear, branched, cyclic or aromatic monovalent olefinic hydrocarbyl group containing up to about 12 carbon atoms, optionally having at least one heteroatom with a hydridosilane having the general formula (III):

$$(R^1O)_{3-n}(R^2)_n Si-H \quad (III)$$

wherein R$^1$ and R$^2$ are each independently a linear or branched alkyl, cycloalkyl or aromatic group containing up to 12 carbon atoms, and where the subscript n is an integer of from 0 to 2 in the presence of at least one dinuclear rhodium complex having the general formula (IV):

$$Rh_2(\mu-X)_a L^1_x L^2_y L^3_z \quad (IV)$$

wherein L$^1$, L$^2$, L$^3$ and X are ligands selected from the group consisting of Cl, Br, I, OH, R^, OR^, OSiR^$_3$, H, CO, R^C(=O)O, O, SR^, S, Se, CO$_3$, SO$_3$, SO$_4$, HPO$_4$, R^PO$_4$, CN, NCO, NCS, NO$_2$, NO$_3$, ClO$_4$, R^SO$_4$, phosphonate, phosphinate, phosphine, amine, imine, amide, ammine, nitrile, heterocycle, β-diketonate, β-diketiminate, amidinate, sulfonate, olefin, ether, thioether, isonitrile, R^NCO, R^NCS, R^OCN, sulfoxide, amineoxide, SO$_2$, CO$_2$, NO, wherein each R^ is independently a linear, branched, cyclic or aromatic hydrocarbon moiety which contains up to 16 carbon atoms and optionally at least one heteroatom, and combinations of two or more of the foregoing ligands which are incorporated into a single ligand, provided that X is a bridging ligand bridging the two rhodium atoms, and where the subscript a is an integer of from 1 to 8, and the subscripts x, v and z are each independently an integer of from 0 to 8 under hydrosilylation conditions.

2. The method of claim 1 wherein R is a divalent alkyl group contain up to 8 carbon and each R$^1$ and R$^2$ is independently a linear or branched alkyl group containing up to 6 atoms.

3. The method of claim 1 wherein the isocyanatosilane produced is selected from the group consisting of 3-isocyanatopropyltrimethoxysilane, 2-isocyanato-1-methylethyltrimethoxysilane, 2-isocyanatopropyltrimethoxysilane, 4-isocyanatobutyltrimethoxysilane, 2-isocyanato-1,1-dimethylethyltrimethoxysilane, 3-isocyanatopropyltriethoxysilane, 2-isocyanato-1-methylethyltriethoxysilane, 2-isocyanatopropyltriethoxysilane, 4-isocyanatobutyltriethoxysilane, 2-isocyanato-1,1-dimethylethyltriethoxysilane, 3-isocyanatopropylmethyldimethoxysilane, 3-isocyanatopropylmethyldiethoxysilane, 2-isocyanato-1-methylethylmethyldimethoxysilane, 2-isocyanatopropylmethyldimethoxysilane, 4-isocyanatobutylphenyldimethoxysilane, and combinations thereof.

4. The method of claim 1 wherein R" is a linear or branched monovalent hydrocarbon containing up to 6 carbon atoms.

5. The method of claim 1, wherein the olefinic isocyanate is selected from the group consisting of vinyl isocyanate, allyl isocyanate, 3-isocyanate-2-methyl-propene, vinylbenzylisocyanate, 1-isocyanate-2-butene, 1-isocyanate-3-methyl-2-butene, 3-isocyanate-1-butene, 3-isocyanate-3-methyl-1-butene, 3-isocyanate-2,3-dimethyl-1-butene, 4-isocyanate-2-methyl-1-butene, 4-isocyanate-3,3-dimethyl-1-butene, 3-isocyanate-3-methyl-1-pentene, 4-isocyanate-4-methyl-1-pentene, 5-isocyanate-1-pentene, 3-isocyanate-1-hexene, 3-isocyanate-5,5-dimethyl-1-hexene, 1-isocyanate-2-heptene and combinations thereof.

6. The method of claim 1 wherein n is 0 or 1.

7. The method of claim 1 wherein the hydridosilane is selected from the group consisting of trimethoxysilane, triethoxysilane, tripropoxysilane, tri-iso-propoxysilane, tributoxysilane, tri-iso-butoxysilane, methyldiethoxysilane, methyldimethoxysilane, dimethylethoxysilane, dimethylmethoxysilane, cyclohexyldi-iso-propoxysilane, phenyldimethoxysilane, and combinations thereof.

8. The method of claim 1 wherein each $L^1$, $L^2$ and $L^3$ is independently selected from the group consisting of CO and 1,5-cyclooctadiene.

9. The method of claim 1 wherein the hydrocarbon moiety is selected from the group consisting of an alkyl, an aryl, and combinations thereof.

10. The method of claim 1 wherein the $L^1$, $L^2$, $L^3$ and X ligands are selected from the group consisting of Cl, Br, I, CO, OH, H, 1,5-cyclooctadiene, ethylene, norbornadiene, 1,5-hexadiene, carboxylate, triphenylphosphine, benzonitrile, benzene, and combinations thereof.

11. The method of claim 1 wherein each of the bridging ligands X are independently selected from the group consisting of Cl, Br, I, OH, R^, OR, OSiR^$_3$, SR^, CO, O, H, carboxylate, and combinations thereof.

12. The method of claim 11 wherein each of the bridging ligands X are selected from Cl, Br, OSiR^$_3$, and combinations thereof.

13. The method of claim 1 where the subscript a is an integer of from 1 to 4.

14. The method of claim 1 wherein the dinuclear rhodium complex is of the general formula (V):

$$[Rh(\mu\text{-}X)L^1_xL^2_yL^3_z]_2 \quad (V)$$

and where $L^1$, $L^2$ $L^3$, and X are as defined and subscripts x, y and z are each an integer from 0 to 4.

15. The method of claim 14 wherein X is selected from the group consisting of Cl, Br, I, OH, R^, OR^, OSiR^$_3$, SR^, CO, O, H, carboxylate, and combinations thereof.

16. The method of claim 14 wherein X is Cl and $L^1$, $L^2$ and $L^3$ are each independently 1,5-cyclooctadiene, norbornadiene, ethylene, cyclooctene, 1,5-hexadiene or CO.

17. The method of claim 1 wherein the dinuclear rhodium complex is of the general formula (VI):

$$L^1_xL^2_yL^3_zRh(\mu\text{-}X)_aRhL^4_uL^5_vL^6_w \quad (VI)$$

wherein $L^1$, $L^2$, $L^3$, and a, x, y and z are as defined, and each of $L^4$, $L^5$ and $L^6$ are as defined for each of $L^1$, $L^2$, $L^3$, and the subscripts u, v and w are each as defined for each of x, y and z.

18. The method of claim 1 wherein the dinuclear rhodium complex is selected from the group consisting of $Rh_2Cl_2(CO)_4$, $Rh_2Cl_2(cod)_2$, $Rh_2Br_2(CO)_4$, $Rh_2I_2(CO)_4$, $Rh_2Cl_2(nbd)_2$, $Rh_2Cl_2(C_2H_4)_4$, $Rh_2Cl_2(coe)_4$, $Rh_2Cl_2(hde)_2$, $Rh_2Cl_2(PPh_3)_4$, $Rh_2Cl_2(CO)_2(PPh_3)_2$, $Rh_2Cl_4(Cp^*)_2$, $Rh_2Br_2(cod)_2$, $Rh_2I_2(cod)_2$, $Rh_2(OH)_2(cod)_2$, $Rh_2(OCH_3)_2(cod)_2$, and $Rh_2(OSiCH_3)_2(cod)_2$.

19. The method of claim 1 wherein the hydrosilylation conditions comprise a temperature of from 50 to about 150° C. and/or a period of time of from about 1 h to about 8 h.

20. The method of claim 1 wherein the isocyanatosilane is produced in a purity of at least 50% based on the weight of the reaction product.

21. The method of claim 1 wherein the product isocyanatosilane is produced having an amount of less than 10% isocyanurate byproduct, based on the weight of the reaction product.

* * * * *